United States Patent [19]

Sum

[11] Patent Number: 5,248,797
[45] Date of Patent: Sep. 28, 1993

[54] METHOD FOR THE PRODUCTION OF 9-AMINO-6-DEMETHYL-6-DEOXYTETRA-CYCLINE

[75] Inventor: Phaik-Eng Sum, Pomona, N.Y.

[73] Assignee: American Cyanamid Company, Stamford, Conn.

[21] Appl. No.: 928,587

[22] Filed: Aug. 13, 1992

[51] Int. Cl.$^5$ ............................................. C07C 235/66
[52] U.S. Cl. ................................................... 552/205
[58] Field of Search ......................................... 552/205

[56] References Cited

U.S. PATENT DOCUMENTS

| | | | |
|---|---|---|---|
| Re. 26,253 | 8/1967 | Petisi | 260/559 |
| Re. 26,271 | 9/1967 | Boothe | 260/559 |
| 3,043,875 | 7/1962 | Beereboom | 260/559 |
| 3,226,436 | 12/1965 | Petisi | 260/559 |
| 3,338,963 | 8/1967 | Petisi et al. | 552/205 |

OTHER PUBLICATIONS

Boothe et al, J. Amer. Chem. Soc., vol. 82, pp. 1253–1254 (1960).
Spencer et al, J. Med. Chem., vol. 6, pp. 405–407 (1963).

*Primary Examiner*—Marianne M. Cintins
*Assistant Examiner*—Kimberly J. Kestler
*Attorney, Agent, or Firm*—Thomas S. Szatkowski

[57] ABSTRACT

The invention relates to a novel method for producing [4S-(4alpha, 12aalpha)]-9-amino-4-(dimethylamino)-1,4,4a,5,5a,6,11,12a-octahydro-3, 10,12,12a-tetrahydroxy-1,11-dioxo-2-naphthacenecarboxamide, hereinafter called 9-amino-6-demethyl-6-deoxytetracycline, which compound is a valuable intermediate for synthesis of tetracyclines.

34 Claims, No Drawings

METHOD FOR THE PRODUCTION OF 9-AMINO-6-DEMETHYL-6-DEOXYTETRACYCLINE

BACKGROUND OF THE INVENTION

1. Field of the Invention

The invention relates to a novel method for producing [4S-(4alpha, 12aalpha)]-9-amino-4-(dimethylamino)-1,4,4a,5,5a,6,11,12a--octahydro-3,10,12,12a-tetrahydroxy-1,11-dioxo-2-naphthacenecarboxamide, hereinafter called 9-amino-6-demethyl-6-deoxytetracycline, which compound is a valuable intermediate for synthesis of tetracyclines.

2. Description of Prior Art

9-Amino-6-demethyl-6-deoxytetracycline is known and useful as a final product and as an intermediate for the synthesis of substituted tetracyclines [U.S. Pat. No. 3,219,671 and 3,226,436; Journal of the American Chemical Society, 82, 1253(1960)].

Prior to the present invention 9-amino-6-demethyl-6-deoxytetracycline was made by nitrating 6-demethyl-6-deoxytetracycline, followed by catalytic reduction to give the desired product (Boothe, J. H. et al., Journal of the American Chemical Society, 82, 1253 (1960)). This method, however, produces a 1:1.5 mixture of 7- and 9-nitro-6-demethyl-6-deoxytetracyclines which are difficult to separate. When conventional techniques of purification are used, such as crystallization or column chromatography, 9-nitro-6-demethyl-6-deoxotetracycline is obtained in 39% yield. Even these conventional purification techniques, however, do not provide 9-nitro-6-demethyl-6-deoxytetracycline with 100% purity. Some 7-nitro-6-demethyl-6-deoxytetracycline is still present as a contaminant.

The 9-nitro so obtained is then reduced to 9-amino-6-demethyl-6-deoxytetracycline. However, due to the previously described difficulty in separating the 7-nitro-6-demethyl-6-deoxytetracycline from the 9-nitro-6-demethyl-6-deoxytetracycline, some 7-amino-6-demethyl-6-deoxytetracycline is also produced.

SUMMARY OF THE INVENTION

It has now been found that 9-amino-6-demethyl-6-deoxytetracycline mineral acid salt, 4, can be made with exceptional purity and yield by reacting 6-demethyl-6-deoxytetracycline, 1, with a halogenating agent in a concentrated mineral acid (U.S. Pat. No. 3,036,129) to yield 7-halogen-6-demethyl-6-deoxytetracyline mineral acid salt, 2, with only minor amounts of the 7,9-dihalogen-6-demethyl-6-deoxytetracycline contaminant. In any event, the 7,9-dihalogen-6-demethyl-6-deoxytetracycline is easily separated, by crystallization, from the desired 7-halogen-6-demethyl-6-deoxytetracycline mineral acid salt,2.

The 7-halogen-6-demethyl-6-deoxytetracycline mineral acid salt, 2, is then nitrated to give 7-halogen-9-nitro-6-demethyl-6-deoxytetracycline mineral acid salt, 3, Because the 7-position is occupied with a halogen, this nitration provides 7-halogen-9-nitro-6-demethyl-6-deoxytetracycline mineral acid salt with exceptional purity and yield.

Preferably, the halogenation and nitration are carried out in one step by reacting 6-demethyl-6-deoxytetracycline, 1, with a halogenating agent in a concentrated mineral acid, followed by the addition of a nitrating reagent to afford substantially pure 7-halogen-9-nitro-6-demethyl-6-deoxytetracycline mineral acid salt, 3.

The 7-halogen-9-nitro-6-demethyl-6-deoxytetracycline mineral acid salt, 3, is in turn reduced to give exceptionally pure 9-amino-6-demethyl-6-deoxytetracycline mineral acid salt, 4, in high yield. This reduction cleaves the halogen and reduces the $NO_2$ all in one step to provide the desired 9-amino-6-demethyl-6-deoxytetracycline mineral acid salt, 4.

DESCRIPTION OF PREFERRED EMBODIMENTS

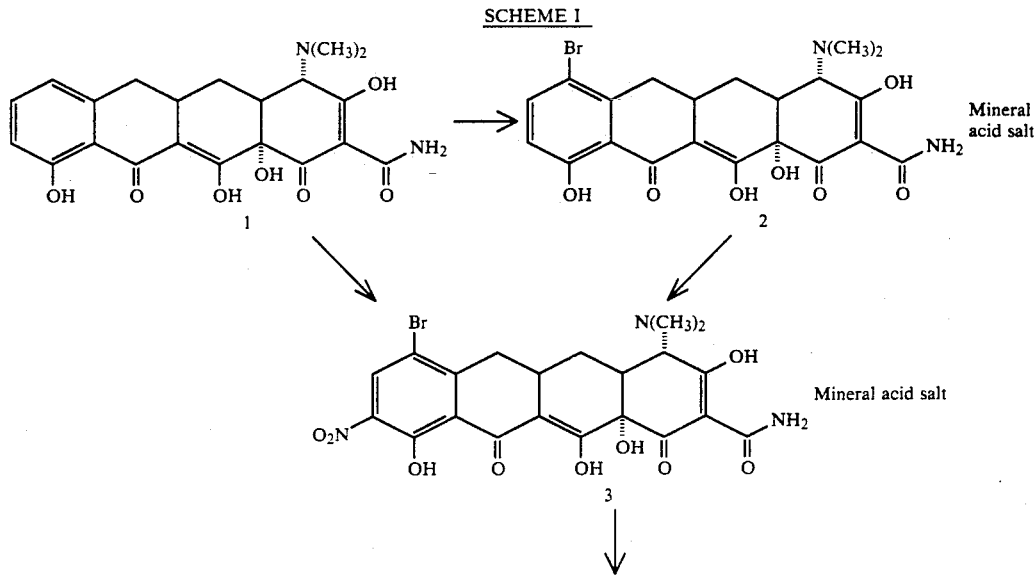

SCHEME I (continued)

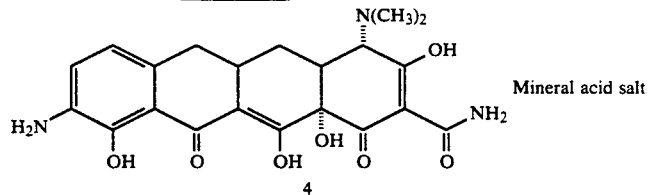

Mineral acid salt

4

Referring to Scheme I, 6-demethyl-6-deoxytetracycline, 1, obtained by literature procedures previously cited, is treated with a halogenating agent such as bromine, N-bromosuccinimide, N-chlorosuccinimide, iodine monochloride or benzyltrimethylammonium dichloroiodate (prepared by the method of Shoji Kajigaeshi et al., Chem Lett, 2109-14 2112(1987)), in a solvent such as a concentrated mineral acid. The reaction is carried out at a temperature between 0° C. and 20° C. until the reaction is complete. The reaction mixture is added dropwise to cold diethyl ether and collected. The crude product is recrystallized to eliminate any 7,9-dihalogen-6-demethyl-6-deoxytetracycline formed and gives pure 7-halogen-6-demethyl-6-deoxytetracycline mineral acid salt, 2.

The pure 7-halogen-6-demethyl-6-deoxytetraccycline mineral acid salt, 2, dissolved in a cold concentrated mineral acid such as concentrated sulfuric acid, is treated at temperatures ranging from about $-15°$ C. to $+15°$ C. with a slight molar excess of a nitrating reagent such as a "mixed acid" or a metal nitrate salt, for from 1-2 hours. The reaction is added dropwise to cold diethyl ether and collected to give 7-halogen-9-nitro-6-demethyl-6-deoxytetracycline mineral acid salt, 3.

Preferably, 6-demethyl-6-deoxytetracycline, is converted directly to 7-halogen-9-nitro-6-demethyl-6-deoxytetracycline mineral acid salt, 3, in one step. 6-Demethyl-6-deoxytetracycline, 1, is dissolved in a cold solvent such as a concentrated mineral acid, and treated with a halogenating agent such as bromine, N-bromosuccinimide, N-chlorosuccinimide or benzyltrimethylammonium dichloroiodate (prepared by the method of Shoji Kajigaeshi et al.). The reaction is stirred for 45 minutes at a temperature between 0° C. and 20° C. A slight molar excess of a solid metal nitrate salt or a "mixed acid" is added and the stirring is continued at between $-15°$ C. and $+15°$ C. for an additional 30 minutes to 2 hours. The reaction is added dropwide to cold diethyl ether. The resulting solid is collected, triturated with an alcohol, filtered and the filtrate is added to diethyl ether. The yellow solid is collected to give pure 7-halogen-9-nitro-6-demethyl-6-deoxytetracycline mineral acid salt, 3, in 93% yield 7-Halogen-9-nitro-6-demethyl-6-deoxytetracycline mineral acid salt, 3, dissolved in a solvent mixture such as 2-methoxyethanol, methanol or ethanol with 1N sulfuric acid or 1N hydrochloric acid, is catalytically reduced with 10-30% by weight of a Group VIII metal catalysts, their salts or rare metal oxides at room temperature under an atmosphere of from 1-40 psi of hydrogen. The reaction is filtered, added slowly to isopropanol and collected to give pure 9-amino-6-demethyl-6-deoxytetracycline mineral acid salt, 4.

This invention will be described in greater detail in conjunction with the following examples.

EXAMPLE 1

[4S-(4alpha, 12a alpha)]-7-Bromo-4-(dimethylamino)-1,4,4a,5,5a,6,11,-12a-octahydro-3,10,12,12a-tetrahydroxy-1,11-dioxo-2-naphthacenecarboxamide sulfate A solution of 4.14. g of 6-demethyl-6-deoxytetracycline, prepared by the described literature procedure, and 1.99 g of N-bromosuccinimide dissolved in 50 ml of concentrated sulfuric acid is stirred at 0° C. for 45 minutes or until solution occurs. The reaction mixture is added dropwise to 2 L of cold diethyl ether. The resulting precipitate is collected and dried. The solid is dissolved in 2-methoxyethanol, triturated with methanol, collected, washed with methanol and diethyl ether and dried to give 6.22 g of crude product. The solid is recrystallized from 2-methoxyethanol and methanol to give 3.1 g of pure product. MS(FAB): m/z 493 (M+H). $^1$H NMR(CD$_3$SOCD$_3$): δ 4.3(s, 1H, 4-H), 6.8(d, 1H, 9-H) and 7.75(d, 1H, 8-H).

EXAMPLE 2

[4S-(4alpha, 12aalpha)]-7-Bromo-4-(dimethylamino)-1,4,4a,5-,5a,6,11,12a-octahydro-3,10,12,12a-tetra-hydroxy-9-nitro-1,11-dioxo-2-naphthacenecarboxamide sulfate To one and one tenth grams of product from Example 1, dissolved in 10 ml of cold concentrated sulfuric acid, is added 1.2 ml of 10% nitric acid in concentrated sulfuric acid. The reaction is stirred at 0° C. for 1½ hours and then added dropwise to 500 ml of ice cold diethyl ether. The resulting solid is collected, washed 3× with diethyl ether and dried under vacuum to give 1.06 g of the desired product (90%). MS(FAB): m/z 538 (M+H).

$^1$HNMR (CD$_3$SOCD$_3$): δ 4.3(s, 1H, 4-H) and 8.48 (s, 1H, 8-H).

EXAMPLE 3

[4S-(4alpha, 12aalpha)]-7-Bromo-4-(dimethylamino)-1,4,4a,5-,5a,6,11,12a-octahydro-3,10,12,12a-tetra-hydroxy-9-nitro-1,11-dioxo-2-naphthacenecarboxamide sulfate To a 0° C. solution of 0.414 g of 6-demethyl-6-deoxytetracycline and 10 ml of concentrated sulfuric acid is added 0.196 g of N-bromosuccinimide. The reaction is stirred at 0° C. for 45 minutes followed by the addition of 0.11 g of solid potassium nitrate. The mixture is stirred, at 0° C., for 30 minutes and then poured into 500 ml of cold diethyl ether. The solid is collected, washed with diethyl ether and dried to give 0.72 g of crude product. The product is purified by trituration with methyl alcohol and isopropyl alcohol, filtered, and the filtrate added to cold diethyl ether. The yellow solid is collected to give 0.59 g of the desired product (93%). MS(FAB): m/z 538 (M+H).

¹HNMR (CD₃SOCD₃): δ 4.3(s, 1H, 4-H) and 8.48 (s, 1H, 8-H).

EXAMPLE 4

[4S-(4alpha)]-9-Amino-4-(dimethylamino)-1,4,4a,5,-5a,6,11,12a-octahydro-3,10,12-12-12a-tetra-hydroxy-1,11-dioxo-2-naphhthacenecarboxamide sulfate A mixture of 1.272 g of product from Example or 2 or 3, dissolved in 50 ml of 2-methoxyethanol and ml of 1N sulfuric acid, and 0.30 g of 10% palladium-on-carbon is hydrogenated in a Parr apparatus for 1 hour at 40 psi. The reaction is filtered thru a pad of diatomaceous earth and the filtrate is poured slowly into 500 ml of isopropanol and diethyl ether (1:4). The yellow solid is collected, washed with diethyl ether and dried to give 1.02 g of desired product (97%).

MS(FAB): m/z 430 (M+H). ¹HNMR (CD₃SOCD₃): δ 4.3(s, 1H, 4-H), 6.8(d, 1H, 7-H) and 7.45(d, 1H, 8-H).

I claim:

1. A process for producing 9-Amino-6-de-methyl-6-deoxytetracycline mineral acid salt which comprises:
    (a) reacting 6-demethyl-6-deoxytetracycline, in cold concentrated mineral acid, with a halogenating agent at a temperature from 0° C. to about 20° C. and recovering 7-halogen-6-demethyl-6-deoxytetracycline mineral acid salt by filtration or recrystallization; and
    (b) reacting the 7-halogen-6-demethyl-6-deoxytetracycline mineral acid salt, in a cold concentrated mineral acid, with a slight molar excess of a nitrating reagent at temperature ranges from −15° C to +15° C. and recovering 7-halogen-9-nitro-6-demethyl-6-deoxytetracycline mineral acid salt by filtration or recrystallization; and
    (c) reducing, at room temperature, the 7-halogen-9-nitro-6-demethyl-6-deoxytetracycline mineral acid salt, in a solvent, with Group VIII metal catalysts, their salts or rare metal oxides at between 1 and 40 psi, isolating the product by dilution in an alcohol and recovering 9-amino-6-demethyl-6-deoxytetracycline mineral acid salt.

2. The process of claim 1 wherein said halogenating agent comprises bromine, N-chlorosuccinimide, N-bromosuccinimide, iodine monochloride or benzyl-trimethylammonium dichloroiodate.

3. The process of claim 2 wherein said halogenating agent comprises N-bromosuccinimide.

4. The process of claim 1 wherein said concentrated mineral acid comprises concentrated sulfuric acid.

5. The process of claim 1 wherein said temperature for step a is maintained at 0° C.

6. The process of claim 1 wherein said 7-halogen-6-demethyl-6-deoxytetracycline mineral acid salt is recovered by filtration.

7. The process of claim 1 wherein said 7-halogen-6-demethyl-6-deoxytetracycline mineral acid salt is recrystallized from a mixture of 2-methoxy-ethanol, methanol and diethyl ether.

8. The process of claim 1 wherein said nitrating reagent comprises a "mixed acid" or a metal nitrate salt.

9. The process of claim 8 wherein said "mixed acid" comprises 1.1 to 1.2 equivalents of 10% nitric acid in concentrated sulfuric acid.

10. The process of claim 1 wherein said mineral acid comprises cold concentrated sulfuric acid.

11. The process of claim 1 wherein said temperature for step b is maintained at 0° C.

12. The process of claim 1 wherein said 7-halogen-9-nitro-6-demethyl-6-deoxytetracycline mineral acid salt is recovered by filtration.

13. The process of claim 1 wherein said Group VIII metal catalyst, their salts or rare earth oxides comprises 10–30% by weight of Pt on activated carbon, Pd on activated carbon, rhodium on activated carbon, ruthenium on activated carbon or iridium on activated carbon.

14. The process of claim 13 wherein said Group VIII metal catalyst comprises 10 to 30% by weight of 10% palladium on activated carbon.

15. The process of claim 1 wherein said solvent for step c is a 5:1 mixture of 2-methoxyethanol:1N sulfuric or hydrochloric acid, methanol:1N sulfuric or hydrochloric acid or ethanol:1N sulfuric or hydro-chloric acid.

16. The process of claim 15 wherein said solvent comprises a 5:1 mixture of 2-methoxyethanol:1N sulfuric acid.

17. The process of claim 1 wherein said 9-Amino-6-demethyl-6-deoxytetracycline mineral acid salt is isolated by dilution with isopropanol.

18. The process of claim 1 wherein said 9-Amino-6-demethyl-6-deoxytetracycline mineral acid salt is recovered by filtration.

19. A process for producing 9-Amino-6-demethyl-6-deoxytetracycline mineral acid salt which comprises:
    (a) reacting 6-demethyl-6-deoxytetracycline, in cold concentrated mineral acid, with a halogenating agent at a temperature from 0° C. to about 20° C. followed by the addition of a slight molar excess of a solid metal nitrate salt or a "mixed acid" at temperature ranges of from −15° C. to +15° C., diluting with a solvent and recovering 7-halogen-9-nitro-6-demethyl-6-deoxytetracycline mineral acid salt; and
    (b) reducing, at room temperature, the 7-halogen-9-nitro-6-demethyl-6-deoxytetracycline mineral acid salt, in a solvent, with Group VIII metal catalysts, their salts or rare metal oxides at between 1 and 40 psi, isolating the product with an alcohol and recovering 9-amino-6- demethyl-6-deoxytetracycline mineral acid salt.

20. The process of claim 19 wherein said halogenating agent comprises bromine, N-bromosuccinimide, N-chlorosuccinimide, iodine monochloride or benzyl-trimethylammonium dichloroiodate.

21. The process of claim 20 wherein said halogenating agent is N-bromosuccinimide.

22. The process of claim 19 wherein said concentrated mineral acid comprises concentrated sulfuric acid.

23. The process of claim 19 wherein said temperature for step a is maintained at 0° C.

24. The process of claim 19 wherein said metal nitrate salt comprises a 10% molar excess of potassium nitrate.

25. The process of claim 19 wherein said "mixed acid" comprises 1.1 to 1.2 equivalents of 10% nitric acid in concentrated sulfuric acid.

26. The process of claim 19 wherein said 7-halogen-9-nitro-6-demethyl-6-deoxytetracycline mineral acid salt is recovered by dilution with diethyl ether.

27. The process of claim 26 wherein said 7-halogen-9-nitro-6-demethyl-6-deoxytetracycline mineral acid salt is purified by trituration with alcohols, dilution of the filtrate with diethyl ether and filtration to collect the resulting pure 7-halogen-9-nitro-6-demethyl-6-deoxytetracycline mineral acid salt.

28. The process of claim 27 wherein said alcohols comprises methyl alcohol and isopropyl alcohol.

29. The process of claim 19 wherein said Group VIII metal catalyst, their salts or rare earth oxides comprises 10-30% by weight of Pt on activated carbon, Pd on activated carbon, rhodium on activated carbon, ruthenium on activated carbon or iridium on activated carbon.

30. The process of claim 29 wherein said Group VIII metal catalyst comprises 10 to 30% by weight of 10% palladium on activated carbon.

31. The process of claim 19 wherein said solvent for step c is a 5:1 mixture of 2-methoxyethanol:1N sulfuric or hydrochloric acid, methanol:1N sulfuric or hydrochloric acid or ethanol:1N sulfuric or hydrochlor acid.

32. The process of claim 31 wherein said solvent comprises a 5:1 mixture of 2-methoxyethanol:1N sulfuric acid.

33. The process of claim 19 wherein said 9-Amino-6-demethyl-6-deoxytetracycline mineral acid salt isolated by dilution with isopropanol.

34. The process of claim 32 wherein said 9-Amino-6-demethyl-6-deoxytetracycline mineral acid salt is recovered by filtration.

* * * * *